United States Patent
Cambronne et al.

(10) Patent No.: US 7,604,662 B2
(45) Date of Patent: Oct. 20, 2009

(54) ENDOPROSTHESES CONTAINING BORIDE INTERMETALLIC PHASES

(75) Inventors: Matthew Cambronne, Mounds View, MN (US); Jonathan S. Stinson, Plymouth, MN (US); Barry O'Brien, Galway (IE)

(73) Assignee: Boston Scientific SciMed, Inc., Maple Grove, MN (US)

( * ) Notice: Subject to any disclaimer, the term of this patent is extended or adjusted under 35 U.S.C. 154(b) by 216 days.

(21) Appl. No.: 11/777,674

(22) Filed: Jul. 13, 2007

(65) Prior Publication Data

US 2009/0018645 A1   Jan. 15, 2009

(51) Int. Cl.
  *A61F 2/06* (2006.01)
(52) U.S. Cl. ............ 623/1.46; 427/2.24; 428/433
(58) Field of Classification Search ...... 623/1.42–1.48; 428/433; 427/2.21–2.25
See application file for complete search history.

(56) References Cited

U.S. PATENT DOCUMENTS

| | | | |
|---|---|---|---|
| 4,800,882 A | 1/1989 | Gianturco | |
| 5,059,205 A | 10/1991 | El-Nounou et al. | |
| 5,091,205 A | 2/1992 | Fan | |
| 5,195,969 A | 3/1993 | Wang et al. | |
| 5,226,909 A | 7/1993 | Evans et al. | |
| 5,270,086 A | 12/1993 | Hamlin | |
| 5,344,402 A | 9/1994 | Crocker | |
| 5,344,426 A | 9/1994 | Lau et al. | |
| 5,366,504 A | 11/1994 | Andersen et al. | |
| 5,443,498 A | 8/1995 | Fontaine | |
| 5,628,787 A | 5/1997 | Mayer | |
| 5,630,840 A | 5/1997 | Mayer | |
| 5,632,840 A | 5/1997 | Campbell | |
| 5,674,242 A | 10/1997 | Phan et al. | |
| 5,755,770 A | 5/1998 | Ravenscroft | |
| 5,780,807 A | 7/1998 | Saunders | |
| 5,824,046 A | 10/1998 | Smith et al. | |
| 5,891,191 A | 4/1999 | Stinson | |
| 5,916,263 A | 6/1999 | Goicoechea et al. | |
| 5,919,570 A | 7/1999 | Hostettler et al. | |
| 5,951,585 A | 9/1999 | Cathcart et al. | |
| 5,957,930 A | 9/1999 | Vrba | |
| 6,120,522 A | 9/2000 | Vrba et al. | |
| 6,123,712 A | 9/2000 | DiCaprio et al. | |
| 6,137,060 A | 10/2000 | Avellanet | |
| 6,238,491 B1 | 5/2001 | Davidson et al. | |
| 6,245,102 B1 * | 6/2001 | Jayaraman | 623/1.15 |
| 6,379,383 B1 | 4/2002 | Palmaz et al. | |
| 6,676,987 B2 | 1/2004 | Zhong | |

(Continued)

FOREIGN PATENT DOCUMENTS

WO   WO 93/19803   10/1993

(Continued)

OTHER PUBLICATIONS

U.S. Appl. No. 60/238,178, filed Oct. 5, 2000, Dicaprio.

(Continued)

*Primary Examiner*—Suzette J Gherbi
(74) *Attorney, Agent, or Firm*—Fish & Richardson P.C.

(57) ABSTRACT

An endoprosthesis including an alloy having a matrix comprising titanium, niobium, or a combination thereof and a plurality of boride intermetallic phases within the matrix.

32 Claims, 3 Drawing Sheets

U.S. PATENT DOCUMENTS

| | | | |
|---|---|---|---|
| 6,726,712 B1 | 4/2004 | Raeder-Devens et al. | |
| 7,001,419 B2 | 2/2006 | DiCaprio et al. | |
| 7,267,686 B2* | 9/2007 | DiMatteo et al. | 623/1.24 |
| 7,429,269 B2* | 9/2008 | Schwammenthal et al. | 623/2.14 |
| 7,442,204 B2* | 10/2008 | Schwammenthal et al. | 623/1.24 |
| 7,445,631 B2* | 11/2008 | Salahieh et al. | 623/2.18 |
| 7,470,285 B2* | 12/2008 | Nugent et al. | 623/2.18 |
| 7,494,507 B2* | 2/2009 | Dixon et al. | 623/17.14 |
| 7,510,575 B2* | 3/2009 | Spenser et al. | 623/2.18 |
| 2002/0032481 A1* | 3/2002 | Gabbay | 623/2.11 |
| 2002/0116046 A1 | 8/2002 | DiCaprio et al. | |
| 2003/0181972 A1 | 9/2003 | Jansen et al. | |
| 2003/0185895 A1 | 10/2003 | Lanphere | |
| 2003/0207975 A1* | 11/2003 | Yadav et al. | 524/435 |
| 2006/0068080 A1* | 3/2006 | Yadav et al. | 427/8 |
| 2006/0224237 A1 | 10/2006 | Furst et al. | |
| 2008/0140052 A1* | 6/2008 | Moller et al. | 604/523 |
| 2008/0154380 A1* | 6/2008 | Dixon et al. | 623/17.16 |
| 2008/0268262 A1* | 10/2008 | Hartig et al. | 428/433 |
| 2008/0289729 A1* | 11/2008 | Pawar et al. | 148/559 |
| 2009/0018644 A1* | 1/2009 | Weber et al. | 623/1.18 |
| 2009/0074836 A1* | 3/2009 | Pawar et al. | 424/423 |
| 2009/0081450 A1* | 3/2009 | Ascher et al. | 428/336 |

FOREIGN PATENT DOCUMENTS

WO     WO 95/30384     11/1995

OTHER PUBLICATIONS

U.S. Appl. No. 09/659,571, filed Sep. 12, 2000, Olson et al.

Chandran et al., "TiB$_w$-Reinforced Ti Composites: Processing, Properties, Application Prospects, and Research Needs," *JOM*, 2004, 9 pages.

Eisenbarth et al., "Biocompatibility of β-stabilizing elements of titanium alloys," *Biomaterials*, 2004, 25:5705-5713.

Gorsse and Miracle, "Mechanical properties of Ti-6A1-4V/TiB composites with randomly oriented and aligned TiB reinforcements," *Acta Materialia*, 2003, 51:2427-2442.

Nano-Phase Boron Titanium Alloys Data Sheet, Crucible Research, one page, date unknown.

Rhenium Alloys, Inc., Tungsten-Rhenium Data Sheet, www.rhenium.com, 1 page, date unknown.

Research Report, Crucible Research, 2005, 3 pages.

"Nanophase P/M titanium as 25% higher strength, stiffness," Data Sheet, 2005, 1 page.

* cited by examiner

ENDOPROSTHESES CONTAINING BORIDE INTERMETALLIC PHASES

TECHNICAL FIELD

This invention relates to endoprostheses, and more particularly to stents.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened, reinforced, or even replaced with a medical endoprosthesis. An endoprosthesis is typically a tubular member that is placed in a lumen in the body. Examples of endoprostheses include stents, covered stents, and stent-grafts.

Endoprostheses can be delivered inside the body by a catheter that supports the endoprosthesis in a compacted or reduced-size form as the endoprosthesis is transported to a desired site. Upon reaching the site, the endoprosthesis is expanded, for example, so that it can contact the walls of the lumen.

The expansion mechanism can include forcing the endoprosthesis to expand radially. For example, the expansion mechanism can include a catheter carrying a balloon, which carries a balloon-expandable endoprosthesis. The balloon can be inflated to deform and to fix the expanded endoprosthesis at a predetermined position in contact with the lumen wall. The balloon can then be deflated, and the catheter withdrawn.

In another delivery technique, the endoprosthesis is formed of an elastic material that can be reversibly compacted and expanded, e.g., elastically or through a material phase transition. During introduction into the body, the endoprosthesis is restrained in a compacted condition. Upon reaching the desired implantation site, the restraint is removed, for example, by retracting a restraining device such as an outer sheath, enabling the endoprosthesis to self-expand by its own internal elastic restoring force.

When the endoprosthesis is advanced through the body, its progress can be monitored, e.g., tracked, so that the endoprosthesis can be delivered properly to a target site. After the endoprosthesis is delivered to the target site, the endoprosthesis can be monitored to determine whether it has been placed property and/or is functioning properly. Methods of monitoring a medical device include X-ray fluoroscopy, computed tomography (CT), and magnetic resonance imaging (MRI).

SUMMARY

An endoprosthesis is disclosed having an alloy that includes (a) a matrix microstructure composed of titanium, niobium, or a combination thereof and (b) at least one boride intermetallic phase within the matrix microstructure.

In some embodiments, the alloy composition can include at least 50 weight percent titanium, niobium, or a combination thereof. For example, in some embodiments, the alloy can include at least 65 weight percent niobium. In some embodiments, the alloy is essentially titanium or essentially niobium. The alloy composition can also include aluminum, vanadium, zirconium, tantalum, molybdenum, iridium, and combinations thereof.

In some embodiments, the at least one boride intermetallic phase can include boride intermetallics of titanium, niobium, tantalum, tungsten, zirconium, molybdenum, iridium, or combinations thereof. For example, the boride intermetallic phase can include titanium boride. In some embodiments, the alloy can include a plurality of boride intermetallic phases within the matrix microstructure. The boride intermetallic phases can have an average length, width, or diameter of between 10 nanometers and 50 microns (e.g., between 1 micron and 40 microns).

In some embodiments, the alloy can include at least 50 weight percent niobium and the plurality of boride intermetallic phases include at least 50 weight percent titanium boride.

In some embodiments, the alloy includes at least 0.1 weight percent boron. The alloy can include up to 1.5 weight percent boron. In some embodiments, the alloy can include up to 0.200 weight percent oxygen. In some embodiments, the alloy can have a Young's modulus of between 14 and 25 msi, a 0.2% offset yield strength of between 50 and 110 ksi, and/or a percent elongation at fracture of between 5 percent to 30 percent.

In some embodiments, the boride intermetallic phases can protrude from a surface of the alloy to create a micro-textured surface. The endoprosthesis can include a drug-eluting polymer coating on the micro-textured surface. In some embodiments, the endoprosthesis can include a surface oxide, nitride, carbide, or combination thereof of the matrix. For example, the endoprosthesis can include a surface layer including an oxide of titanium, an oxide of niobium, or a combination thereof.

In some embodiments, the alloy can overlie a base including stainless steel, platinum enhanced stainless steel, nitinol, or Co—Cr alloy.

In some embodiments, the endoprosthesis can include a radiopaque material. For example, the endoprosthesis can include an outer layer having the radiopaque material or the alloy formulation can include the radiopaque material. In some embodiments, the alloy includes between 30 to 50 weight percent of the radiopaque material. The radiopaque material can include tantalum, iridium, or a combination thereof.

In some embodiments, the endoprosthesis is a stent. For example, the stent can be a balloon-expandable stent. In some embodiments, a stent can have a wall thickness of between 0.0015 and 0.0060 inches. The stent can have a diameter recoil of less than 8 percent upon balloon expansion to 3.2 mm diameter. The stent can require 0.10 to 0.50 Newtons force per millimeter of stent length to compress it from an initial balloon expanded diameter of 3.2 mm to 2.75 mm diameter within V-shaped platens of a stent compression tester.

Other aspects, features, and advantages will be apparent from the detailed description and from the claims.

DETAILED DESCRIPTION

Figure 1:
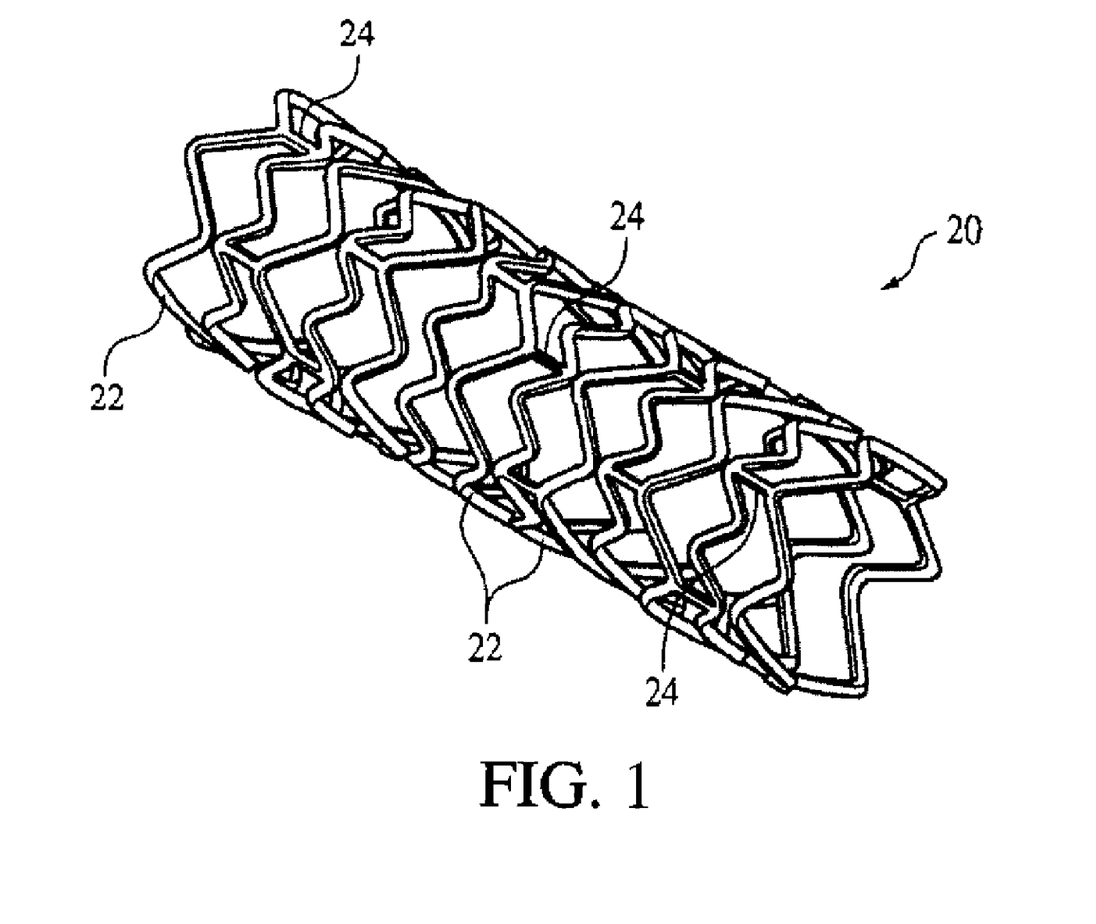
FIG. 1 is a perspective view of an embodiment of an expanded stent.

Referring to FIG. 1, a stent 20 can have the form of a tubular member defined by a plurality of bands 22 and a plurality of connectors 24 that extend between and connect adjacent bands. For example, the stent 20 in FIG. 1 can be a balloon-expandable stent. During use, bands 22 can be expanded from an initial, small diameter to a larger diameter to contact stent 20 against a wall of a vessel, thereby maintaining the patency of the vessel. Connectors 24 can provide stent 20 with flexibility and conformability that allow the stent to adapt to the contours of the vessel.

Any or all of the portions of stent 20 can include a boron containing alloy 26. By alloying boron with titanium, niobium, or an alloy including titanium or niobium, an alloy is obtained that includes precipitated boride intermetallic phases 30 within a matrix 28. The boride intermetallic phases 30 act as stiffeners, giving increased elastic modulus and therefore better recoil performance than titanium and/or niobium would otherwise provide.

The alloy can include at least 50 weight percent titanium, niobium, or a combination thereof. In some embodiments, the alloy can include at least 65 weight percent niobium, essentially pure niobium, or essentially pure titanium. The alloy can also include aluminum, vanadium, zirconium, tantalum, molybdenum, iridium, or combinations thereof. For example, boron can be alloyed with commercially pure or alloyed titanium or niobium materials, such as C.P. Ti, Ti-6Al-4V, C.P. Nb, Nb-1Zr, Nb-28Ta-3.5W-1.3Zr, Ti-6Al-7Nb, Ti-25Nb, Ti-15Mo, or Ti-13Nb-13Zr. Although the formation of the boride intermetallic phases can somewhat alter the composition of the matrix from the remainder of the alloying material, the matrix will often have a composition similar to the composition of the non-boron alloying materials. In some embodiments, the alloy can further include a radiopaque metal, such as tantalum, iridium, or a combination thereof. In some embodiments, the alloy can include between 30 and 50 weight percent of the radiopaque metal.

The boride intermetallic phases 30 can include boride intermetallics of titanium, niobium, tantalum, tungsten, zirconium, molybdenum and/or iridium. For example, the boride intermetallic phases 30 can include titanium boride.

The boride intermetallic phases 30 can have an average length, width, or diameter of between 10 nanometers and 50 microns. In some embodiments, the average length, width, or diameter of the boride intermetallic phases can be between 1 micron and 40 microns. The boride intermetallic phases 30 can be in the form of whiskers, platelets, or globules. Boron has limited solubility in titanium and niobium, which means that relatively low amounts of boron are needed in order to get a significant population of precipitated boron intermetallic phases 30. For example, the alloy 26 can include as little as 0.1 weight percent boron. In some embodiments, the alloy can include up to 1.5 weight percent boron. In some embodiments, the alloy can include an oxygen concentration of less than or equal to 0.200 weight percent, as measured by the inert gas fusion technique.

The boride intermetallic phases 30 can enhance the mechanical properties of the matrix 28. Because boride intermetallics, such as titanium boride, are relatively thermodynamically stable compounds, diffusion zones do not generally form around the boride intermetallic phases 30. Diffusion zones can defeat the modulus enhancement. For example, the alloy 26 can have:

(a) an elongation at break of between 5 and 30 percent, as measured according to ASTM E8 with gage marks on a 1.0-inch gage length, 0.05 inch/minute strain rate;

(b) a 0.2% offset yield strength (YS) of 50-110 ksi, as measured according to ASTM E8; and/or (c) a Young's modulus of elasticity of between 14 msi and 25 msi, as measured according to ASTM E8.

The mechanical properties that the alloy 26 provides can allow a stent to be formed with reduced wall thickness relative to alloys without the boride precipitates without compromising the performance of the stent. A thinner walled stent can be more easily delivered through a tortuous path, can be implanted in a smaller bodily vessel, and/or can allow more fluid flow through the stent. In some embodiments, the wall thickness of a finished stent made using the alloy 26 can be between 0.0015 inches and 0.0060 inches thick. A stent made of one of the described alloys can also have a diameter recoil of less than 8 percent upon balloon expansion to 3.2 mm diameter. A stent made of one of the described alloys can require between 0.10 to 0.50 Newtons force per millimeter of stent length to compress it from an initial balloon expanded diameter of 3.2 mm to 2.75 mm diameter within compression tester V-shaped platens.

Figure 2:
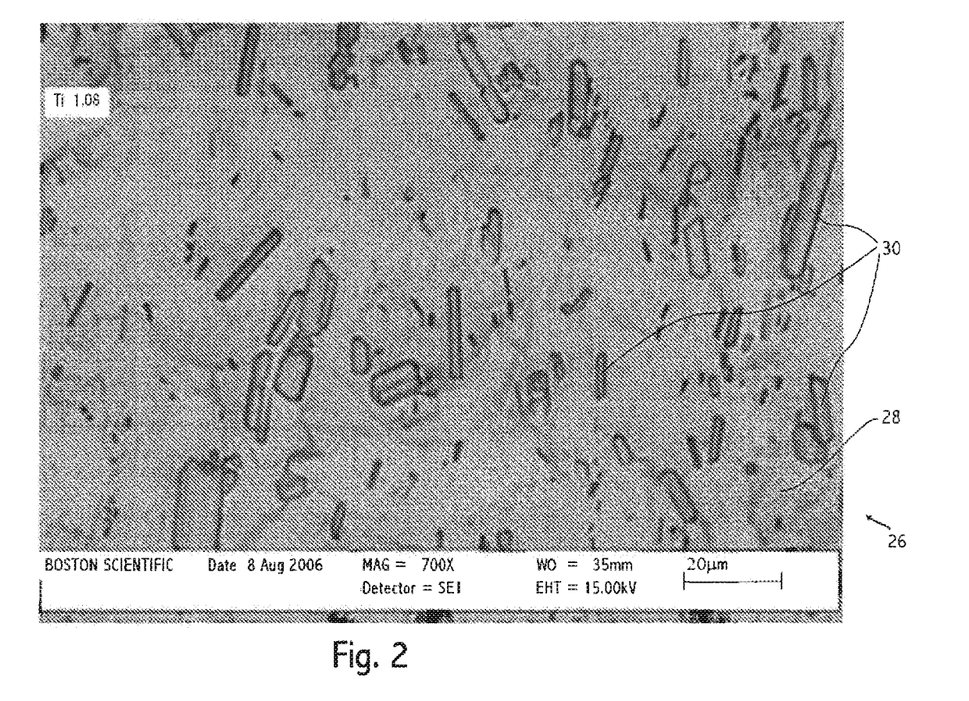
FIG. 2 is an SEM secondary electron image of an embodiment of alloy.

FIG. 2 depicts an SEM secondary electron image captured at 700× magnification of an alloy 26 which includes a primarily titanium matrix 28 and titanium boride intermetallic phases 30. The titanium-boron alloy in FIG. 2 includes 1.09 weight percent boron with the remainder being essentially titanium, with the usual impurities present in commercially pure ("CP") titanium. Table I, below, compares the properties of titanium-boron alloys having 1.09 and 1.41 weight percent boron with other titanium materials that lack boron intermetallic phases.

TABLE I

| Material | Modulus, msi | Yield Strength, ksi | Ultimate Strength, ksi | Elongation, % |
|---|---|---|---|---|
| C.P. Grade 1 Ti ($O_2$ < 0.18) | 14.5 | 34.8 | 47.9 | 30 |
| C.P. Grade 2 Ti ($O_2$ < 0.25) | 14.8 | 49.3 | 62.4 | 28 |
| Ti—6Al—4V ($O_2$ < 0.20) | 16.5 | 128 | 138 | 14 |
| Ti—1.09B ($O_2$ < 0.097) | 18.4-18.8 | 64.5-78.9 | 91.9-107.0 | 17-20 |
| Ti—1.41B ($O_2$ < 0.119) | 18.6-20.9 | 89.9-105.7 | 123.0-147.6 | 7-9 |

In some embodiments, a surface of the alloy can be treated to produce a micro-textured surface having protruding boride intermetallic phases 30. A micro-textured surface can be formed by electropolishing or electroetching a surface of the alloy because the non-conductive boride intermetallic phases 30 are not dissolved as readily as the matrix 28 material during electroetching or electropolishing. This micro-textured surface can increase the adhesion of a drug-eluting polymer coating on the micro-textured surface, such as those described in U.S. Pat. No. 5,674,242, U.S. Ser. No. 09/895,415, filed Jul. 2, 2001, and U.S. Ser. No. 10/232,265, filed Aug. 30, 2002. The therapeutic agents, drugs, or pharmaceutically active compounds can include, for example, anti-thrombogenic agents, antioxidants, anti-inflammatory agents, anesthetic agents, anti-coagulants, and antibiotics. The micro-textured surface can also increase the adhesion of other surface coatings and treatments, or may provide a more permanent placement of a stent when inserted into a body passageway. For example, the surface of the titanium-boron alloy 26 shown in FIG. 2 has been etched to produce a micro-textured surface.

In some embodiments, a stent may be produced by applying a coating of the alloy 26 to a surface of stainless steel, a platinum enhanced stainless steel, such as PERSS®, nitinol, Co—Cr alloy, or other stent material. The coating can be a thin coating deposited by a thermal stray process. The outer surface of the alloy 26 can then be etched or polished to produce a micro-textured surface.

Another application for the micro-textured surface would be for use as an embolic surface in intravascular occlusion coils, which are implanted in intracranial arteries and are intended to cause thrombosis and occlusion to prevent blood flow to an aneurysm downstream. Thrombosis, blood platelet adhesion, more readily occurs on rough surfaces. The micro-textured surface can be advantageous for occlusion devices because it could facilitate thrombosis.

Alloy 26 can be produced by a number of methods. The alloy can be produced by an alloying method to ensure that the distribution of the boride intermetallic throughout the material is homogeneous. One method of manufacturing the alloy 26 is by a powder metallurgy process. For example, raw materials can be weighed and combined according to the desired final composition. When forming a melting furnace charge, the alloying elements can either be separately added as individual elemental constituents or can be added as a preformed binary, ternary, or other master alloys. The charge then may be vacuum induction melted to form a homogeneous liquid metal bath. The boron is in solution when the materials are melted (in the liquid phase). The bath then can be tapped so that the liquid metal streams out of the bottom of a melt crucible. Inert gas jets may spheroidize the liquid metal, a process often called atomization. As the spherodized liquid metal falls, it can rapidly solidify and form fine, spherical powder particles, so as to produce power particles that individually contain the complete and homogeneous final composition. The boride intermetallic phases 30 then precipitate out as the alloy solidifies and cools.

When producing the alloy 26, boride intermetallic phases 30 may be formed with any or all of the primary alloying constituents. For example, boron can be alloyed with commercially pure or alloyed titanium or niobium materials, such as C.P. Ti, Ti-6Al-4V, C.P. Nb, Nb-1Zr, Nb-28Ta-3.5W-1.3Zr, Ti-6Al-7Nb, Ti-25Nb, Ti-15Mo, or Ti-13Nb-13Zr. This would result in boride intermetallics of titanium, niobium, aluminum, vanadium, zirconium, tantalum, and/or molybdenum. For example, when alloying boron with Nb-28Ta-3.5W-1.3Zr, the boride intermetallics could be of niobium, tantalum, tungsten, and/or zirconium. Titanium can be a preferential boride intermetallic former in the presence of niobium and other alloying elements, such as Ta, W, and/or Zr, thereby allowing for the creation of a microstructure containing a niobium-based matrix with the boride intermetallic phases comprising at least 50 weight percent titanium boride. In some embodiments, the alloy 26 includes a matrix 26 that includes at least 50% niobium and a plurality of boride intermetallic phases 30 that include at least 50 weight percent titanium boride. For example, by alloying Nb-28Ta-3.5W-1.3Zr with boron and titanium, an alloy 26 can be created having a matrix 28 that includes about 65% niobium. The boride intermetallic phases 30 can also have at least 50 weight percent titanium boride. Another option is to alloy C.P. Niobium, boron, and between 0.1 weight percent and 1.5 weight percent titanium to create an alloy 26 having a niobium matrix 28 and titanium boride intermetallic phases 30.

Following atomization, the alloy powder can be hot-isostatically pressed ("HIP'ed") into a rod or hollow rod shape. The HIP'ing process can metallurgically bond the alloy powder and densify the material. The size of the atomized particles can impact the size of the boride intermetallic phases 30. For example, the atomized powder may be between less than about 150 microns, or can even be less than about 50 microns. The size of the atomized powder can impact the size of the boride intermetallic phases 30 resulting from the HIPing process; a smaller powder size is believed to result in smaller boride intermetallic phases 30. A HIP'ed rod can then be hot-forged, rolled, or extruded to produce a wrought microstructure. The as-HIP'ed or wrought rod (solid or hollow) can then be used as feed stock for stent seamless tube drawing operations, can be rolled into thin strip which is subsequently rolled and welded to form stent tubing, or can be drawn into fine wire. In other embodiments, the atomized alloy powder could be formed into a tubing feed stock by pressing and sintering, cold compaction, extrusion, forging, plasma spray deposition, laser forming, or combinations thereof.

Figure 3A:
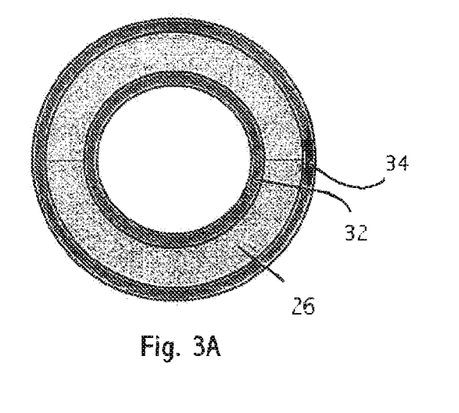
FIGS. 3A and 3B are embodiments of the alloy combined with one or more layers of radiopaque material.
Figure 3B:
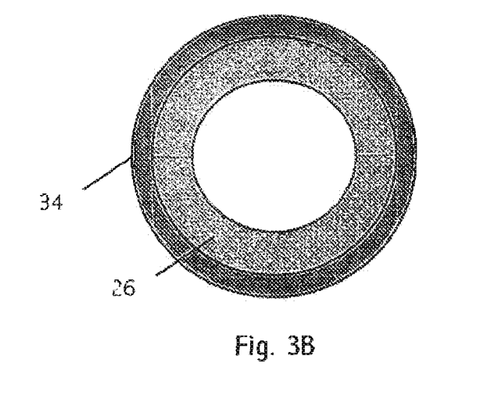

In some embodiments, such as those shown in FIGS. 3A and 3B, a stock material used for making a stent can have inner 32 and/or outer 34 layers of a second and/or third material. The second and/or third materials can have higher densities to improve the radiopacity of the composite material. This can be achieved by using powder metallurgy and HIP processes. One method to combine the alloy 26 with one or more layers of radiopaque material 32 or 34 would be to create one or more hollow cylinders of the radiopaque material 32 or 34 and HIP the alloy powder adjacent to the one or more hollow cylinders of radiopaque material 32 or 34. This can create a metallurgical bond between the alloy 26 and the radiopaque material 32 or 34.

In the embodiment shown in FIG. 3A, the alloy 26 is formed between two hollow cylinders 32 and 34. In some embodiments, one or both of the inner cylinder 32 and the outer cylinder 34 are radiopaque. In embodiments not shown, the inner layer 32 may be a bar rather than a hollow cylinder. For example, the inner and outer cylinder can both be tantalum and the alloy 26 can include a matrix 28 of primarily titanium with titanium boride intermetallic phases 30. In the embodiment shown in FIG. 3B, the alloy 26 is formed on the interior of a hollow cylinder 34 of radiopaque material. In embodiments not shown, the alloy 26 may completely fill the interior of the interior of the hollow cylinder 34 to form a bar rather than a hollow tube. For example, the cylinder 34 can be tantalum and the alloy 26 can include a matrix 28 of primarily titanium with titanium boride intermetallics 30.

The two or three layered bar/hollow tube can be used as feed stock for stent seamless tube drawing operations, such as that described below. In any of the embodiments, the materials and thickness of the cylinders 32 and 34 and the alloy 26 can be designed such that once the multilayered bar/hollow tube is drawn into stent tubing, stents cut from that tubing would have an appropriate overall density (radiopacity) for fluoroscopic and CT imaging. The materials can also be chosen to provide biocompatibility. For example, tantalum has a high modulus (27 msi), is known to be highly biocompatible, and has a much higher density than titanium (Ta 16.65 g/cc vs. Ti 4.51 g/cc).

Figure 4:
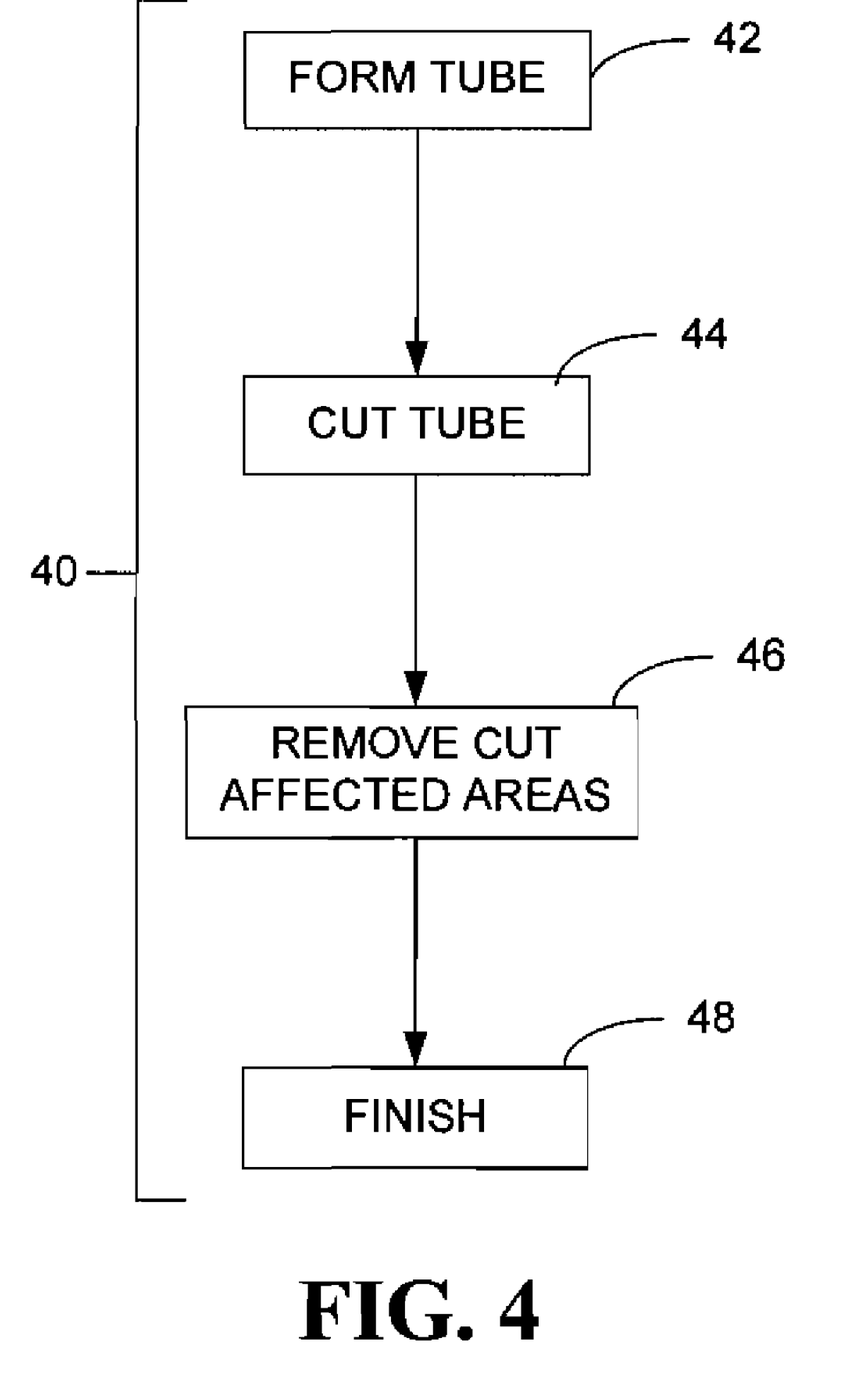
FIG. 4 is a flow chart of an embodiment of a method of making a stent.

FIG. 4 shows an example of a method 40 of making a stent 20. As shown, method 40 can include forming a tube (step 42) including alloy 26 that makes up the tubular member of stent 20. The tube can be subsequently cut to form bands 22 and connectors 24 (step 44) to produce an unfinished stent; e.g, by laser or chemical machining. Areas of the unfinished stent affected by the cutting can be subsequently removed (step 46). The unfinished stent can be finished to form stent 20 (step 48).

Bands 22 and connectors 24 of stent 20 can be formed, as shown in FIG. 1, by cutting the tube (step 44). Selected portions of the tube can be removed to form bands 22 and connectors 24 by laser cutting, as described in U.S. Pat. No. 5,780,807, hereby incorporated by reference in its entirety. In certain embodiments, during laser cutting, a liquid carrier, such as a solvent or an oil, can flow through the lumen of the tube. The carrier can prevent dross formed on one portion of the tube from re-depositing on another portion, and/or reduce formation of recast material on the tube. Other methods of removing portions of the tube can be used, such as mechanical machining (e.g., micro-machining), electrical discharge machining (EDM), chemical etching, and photoetching (e.g., acid photoetching).

In some embodiments, after bands 22 and connectors 24 are formed, areas of the tube affected by the cutting operation above can be removed (step 46). For example, laser machining of bands 22 and connectors 24 can leave a surface layer of melted and resolidified material and/or oxidized metal that can adversely affect the mechanical properties and performance of stent 20. The affected areas can be removed mechanically (such as by grit blasting or honing) and/or chemically (such as by etching or electropolishing). In some embodiments, the tubular member can be near net shape configuration after step 46 is performed. "Near-net size" means that the tube has a relatively thin envelope of material that is removed to provide a finished stent. In some embodiments, the tube is formed less than about 25 percent oversized.

The unfinished stent can then be finished to form stent 20. The unfinished stent can be finished, for example, by electropolishing or electroetching. In some embodiments, the electropolishing or electroetching of the stent will result in a micro-textured surface. The non-conductive boride intermetallics 30 are not dissolved as readily as the matrix 28 material (e.g., titanium) during electroetching or electropolishing; thus the boride intermetallic phases 30 can remain as protrusions on the finished stent surface. In some embodiment, the stent surface can be coated with a polymer or metal. A micro-textured surface can promote the adhesion of a polymer or metal coating relative to a smoothly polished surface.

Other finishing operations can include the conversion of some of or all of the surfaces into oxides, nitrides, carbides, or combinations thereof. For example, the surface could be heated in air atmosphere to a temperature of 650 to 980° C. for 2 to 10 minutes. During this treatment, the titanium surface react with oxygen in the air at elevated temperature and form titanium oxide. This layer can grow from the original matrix 28 surface and reduce the difference in profile between the boride intermetallic phase 30 protrusions and the original matrix 28 surface; thereby making it smoother. If the matrix comprises titanium and the air atmosphere was supplemented with a partial pressure of nitrogen, titanium oxynitride can form on the titanium matrix 28 instead of titanium oxide. Titanium oxynitride may have a pro-healing response to minimize restenosis. An alternate method is to use electrochemical anodizing to build the oxide layer rather than thermal treatment.

Since the unfinished stent can be formed to near-net size, relatively little of the unfinished stent needs to be removed to finish the stent. As a result, further processing (which can damage the stent) and costly materials can be reduced. In some embodiments, about 0.0001 inch of the stent material can be removed by chemical milling and/or electropolishing to yield a stent.

In some embodiments, the stock material can be drawn through a series of dies with progressively smaller circular openings to plastically deform the member to a targeted size and shape. In some embodiments, a hollow tubular segment of stock material can be shaped by pilgering, fixed mandrel drawing, floating plug drawing, or a combination thereof. The resulting hollow tubular member can have an outer diameter of between 0.050 inches and 0.090 inches and a wall thickness of between 0.0030 inches and 0.0060 inches. The plastic deformation strain can alter the properties of the alloy, for example, by breaking apart the boride intermetallic phases 30.

Stent 20 can be of a desired shape and size (e.g., coronary stents, aortic stents, peripheral vascular stents, gastrointestinal stents, urology stents, and neurology stents). Depending on the application, stent 20 can have a diameter of between, for example, 1 mm to 46 mm. In certain embodiments, a coronary stent can have an expanded diameter of from 2 mm to 6 mm. In some embodiments, a peripheral stent can have an expanded diameter of from 5 mm to 24 mm. In certain embodiments, a gastrointestinal and/or urology stent can have an expanded diameter of from 6 mm to about 30 mm. In some embodiments, a neurology stent can have an expanded diameter of from about 1 mm to about 12 mm. An abdominal aortic aneurysm (AAA) stent and a thoracic aortic aneurysm (TAA) stent can have a diameter from about 20 mm to about 46 mm. Stent 20 can be balloon-expandable, self-expandable, or a combination of both (e.g., U.S. Pat. No. 5,366,504).

For example, the alloys described above could be used to produce BE coronary stents having a 0.0030 inch wall thickness, a 0.080 inch outer diameter, and a 0.074 inch inner diameter. Such stents can be produced by melting matrix and boron materials in a VIM furnace with an argon gas atomization fixture on the outlet of the VIM crucible. The atomized powder can be hot-isostatically pressed using conventional alloy HIP process parameters to form a dense preform in the shape of a hollow rod. After machining to remove alpha case (e.g., titanium oxide), the hollow rod can have an outer diameter of 0.8 to 1.2 inches and an inner diameter of 0.4 to 0.6 inches and a length of 6 to 9 inches. The hollow rod can be hot-extruded to reduce the wall thickness by 20 to 80 percent. The tube can be reduced in size via fixed mandrel or floating plug tube drawing operations with intermediate annealing steps to the final configuration of 0.080" outer diameter and 0.070" inner diameter. The stent tubing can be subjected to laser machining to cut the stent struts and connector geometry in the wall. Electrochemical etching and polishing can be used to remove the laser-affected layer of material, to produce the finished stent dimensions, and to produce the surface texture with microscopic boride particle protrusions. Small tantalum or platinum radiopaque marker bands can be secured onto the stent struts. A drug-eluting polymer coating can be applied to the stent surface. The stent can be crimped onto a balloon catheter, packaged, and sterilized.

A Ti-0.5B BE coronary stent of the above dimensions would have a diameter recoil of less than 6 percent upon balloon expansion to 3.2 mm diameter and would require 0.10 to 0.30 Newtons force per millimeter of stent length to compress it from an initial balloon expanded diameter of 3.2 mm to 2.75 mm diameter within compression tester V-shaped platens. The tensile properties of the Ti-0.5B annealed stent tubing would be 17-19 msi Young's modulus, 40-60 ksi 0.2% offset yield strength, 65-85 ksi ultimate tensile strength, and >20 percent elongation.

A Ti-1.1B BE coronary stent of the above dimensions would have a diameter recoil of less than 8 percent upon balloon expansion to 3.2 mm diameter and would require 0.20 to 0.40 Newtons force per millimeter of stent length to compress it from an initial balloon expanded diameter of 3.2 mm to 2.75 mm diameter within compression tester V-shaped platens. The tensile properties of the Ti-1.1B annealed stent tubing would be 18-20 msi Young's modulus, 55-75 ksi 0.2% offset yield strength, 80-100 ksi ultimate tensile strength, and >15 percent elongation.

A Ti-1.4B BE coronary stent of the above dimensions would have a diameter recoil of less than 6 percent upon balloon expansion to 3.2 mm diameter and would require 0.30 to 0.50 Newtons force per millimeter of stent length to compress it from an initial balloon expanded diameter of 3.2 mm to 2.75 mm diameter within compression tester V-shaped platens. The tensile properties of the annealed Ti-1.4B stent tubing would be 19-21 msi Young's modulus, 75-95 ksi 0.2% offset yield strength, 100-120 ksi ultimate tensile strength, and >10 percent elongation.

A Ti-45Ta-1.2B BE coronary stent of the above dimensions would have a diameter recoil of less than 8 percent upon balloon expansion to 3.2 mm diameter and would 0.20 to 0.40 Newtons force per millimeter of stent length to compress it from an initial balloon expanded diameter of 3.2 mm to 2.75 mm diameter within compression tester V-shaped platens. The tensile properties of the annealed Ti-45Ta-1.2B stent tubing would be 14-16 msi Young's modulus, 65-85 ksi 0.2% offset yield strength, 110-130 ksi ultimate tensile strength, and >10 percent elongation.

A Nb-1.2B BE coronary stent of the above dimensions would have a diameter recoil of less than 8 percent upon balloon expansion to 3.2 mm diameter and would require 0.10 to 0.30 Newtons force per millimeter of stent length to compress it from an initial balloon expanded diameter of 3.2 mm to 2.75 mm diameter within compression tester V-shaped platens. The tensile properties of the annealed stent tubing would be 16-18 msi Young's modulus, 30-50 ksi 0.2% offset yield strength, 50-70 ksi ultimate tensile strength, and >15 percent elongation.

In use, stent 20 can be used, e.g., delivered and expanded, using a catheter delivery system. Catheter systems are described in, for example, Wang U.S. Pat. No. 5,195,969, Hamlin U.S. Pat. No. 5,270,086, and Raeder-Devens, U.S. Pat. No. 6,726,712. Stents and stent delivery are also exemplified by the Sentinol® system, available from Boston Scientific Scimed, Maple Grove, Minn.

In some embodiments, stent 20 can be formed by fabricating a wire including the alloy 26, and knitting and/or weaving the wire into a tubular member.

Stent 20 can be a part of a covered stent or a stent-graft. In other embodiments, stent 20 can include and/or be attached to a biocompatible, non-porous or semi-porous polymer matrix made of polytetrafluoroethylene (PTFE), expanded PTFE, polyethylene, urethane, or polypropylene.

The alloy described herein can be used to form other endoprostheses. For example, the alloy can be used to form a guideword or a hypotube. A guidewire can have portions including different concentrations of particles to provide a flexible distal section for good trackability and a stiff proximal section for good pushability. The alloy can be used to form metal staples and wires used for wound closure.

All publications, references, applications, and patents referred to herein are incorporated by reference in their entirety.

Other embodiments are within the claims.

What is claimed is:

1. An endoprosthesis comprising an alloy that includes
   (a) a matrix microstructure comprising titanium, niobium, or a combination thereof; and
   (b) at least one boride intermetallic phase within the matrix, wherein the alloy comprises at least 0.1 weight percent boron.

2. The endoprosthesis of claim 1, wherein the alloy comprises at least 50 weight percent titanium, niobium, or a combination thereof.

3. The endoprosthesis of claim 1, wherein the alloy consists essentially of titanium.

4. The endoprosthesis of claim 1, wherein the alloy consists essentially of niobium.

5. The endoprosthesis of claim 1, wherein the at least one boride intermetallic phase comprises boride intermetallics of a metal selected from the group consisting of titanium, niobium, tantalum, tungsten, zirconium, molybdenum, iridium, and combinations thereof.

6. The endoprosthesis of claim 1, wherein the at least one boride intermetallic phase comprises titanium boride.

7. The endoprosthesis of claim 1, further comprising a plurality of boride intermetallic phases within the matrix.

8. The endoprosthesis of claim 7, wherein the plurality of boride intermetallic phases have an average length, width, or diameter of between 10 nanometers and 50 microns.

9. The endoprosthesis of claim 8, wherein the average length, width, or diameter of the boride intermetallic phases is between 1 micron and 40 microns.

10. The endoprosthesis of claim 1, wherein the alloy comprises up to 1.5 weight percent boron.

11. The endoprosthesis of claim 1, wherein the alloy comprises at least 50 weight percent niobium and the plurality of boride intermetallic phases comprise at least 50 weight percent titanium boride.

12. The endoprosthesis of claim 1, wherein the alloy comprises up to 0.200 weight percent oxygen.

13. The endoprosthesis of claim 1, further comprising a radiopaque material.

14. The endoprosthesis of claim 13, comprising an outer layer comprising the radiopaque material.

15. The endoprosthesis of claim 13, wherein the matrix comprises the radiopaque material.

16. The endoprosthesis of claim 15, wherein the matrix comprises between 30 to 50 weight percent of the radiopaque material.

17. The endoprosthesis of claim 13, wherein the radiopaque material comprises tantalum, iridium, or a combination thereof.

18. The endoprosthesis of claim 1, further comprising a surface layer comprising an oxide of titanium, an oxide of niobium, or a combination thereof.

19. The endoprosthesis of claim 1, wherein the endoprosthesis is a stent.

20. The endoprosthesis of claim 19, wherein the stent is a balloon-expandable stent.

21. The endoprosthesis of claim 19, wherein the stent comprises a wall thickness of between 0.0015 and 0.0060 inches.

22. The endoprosthesis of claim 19, wherein the stent comprises diameter recoil of less than 8 percent upon balloon expansion to 3.2 mm diameter.

23. The endoprosthesis of claim 19, wherein the stent requires 0.10 to 0.50 Newtons force per millimeter of stent length to compress it from an initial balloon expanded diameter of 3.2 mm to 2.75 mm diameter within a V-shaped platens compression tester.

24. An endoprosthesis comprising an alloy that includes
   (a) a matrix microstructure comprising titanium, niobium, or a combination thereof, wherein the alloy comprises at least 65 weight percent niobium; and
   (b) at least one boride intermetallic phase within the matrix.

25. The endoprosthesis of claim 1, wherein the alloy further comprises a metal selected from the group consisting of aluminum, vanadium, zirconium, tantalum, molybdenum, iridium, and combinations thereof.

26. An endoprosthesis comprising an alloy that includes
   (a) a matrix microstructure comprising titanium, niobium, or a combination thereof; and
   (b) at least one boride intermetallic phase within the matrix, wherein boride intermetallic phases protrude from a surface of the alloy to create a micro-textured surface.

27. The endoprosthesis of claim 26, further comprising a drug-eluting polymer coating on the micro-textured surface.

28. The endoprosthesis of claim 1, further comprising an oxide, nitride, carbide, or combination thereof of the matrix on the surface of the finished part.

29. The endoprosthesis of claim 1, wherein the alloy has a Young's modulus of between 14 and 25 msi.

30. An endoprosthesis comprising an alloy that includes
   (a) a matrix microstructure comprising titanium, niobium, or a combination thereof; and
   (b) at least one boride intermetallic phase within the matrix, wherein the alloy has a 0.2% offset yield strength of between 50 and 110 ksi.

31. The endoprosthesis of claim 1, wherein the alloy has a percent elongation at fracture of between 5 percent to 30 percent.

32. The endoprosthesis of claim 1, wherein the alloy overlies a base comprising stainless steel, platinum enhanced stainless steel, nitinol, or Co—Cr alloy.

* * * * *